(12) United States Patent
Ahmed et al.

(10) Patent No.: US 10,874,316 B2
(45) Date of Patent: Dec. 29, 2020

(54) SYSTEMS AND METHODS FOR ADAPTIVE SENSORS CALIBRATION

(71) Applicant: Tata Consultancy Services Limited, Mumbai (IN)

(72) Inventors: Nasimuddin Ahmed, Kolkata (IN); Arijit Chowdhury, Kolkata (IN); Avik Ghose, Kolkata (IN); Tapas Chakravarty, Kolkata (IN); Shalini Mukhopadhyay, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 343 days.

(21) Appl. No.: 15/937,611

(22) Filed: Mar. 27, 2018

(65) Prior Publication Data

US 2018/0317782 A1  Nov. 8, 2018

(30) Foreign Application Priority Data

Apr. 25, 2017  (IN) .............................. 201721014655

(51) Int. Cl.
*A61B 5/0295* (2006.01)
*A61B 5/1455* (2006.01)
(Continued)

(52) U.S. Cl.
CPC ........ *A61B 5/0295* (2013.01); *A61B 5/02416* (2013.01); *A61B 5/02427* (2013.01);
(Continued)

(58) Field of Classification Search
None
See application file for complete search history.

(56) References Cited

U.S. PATENT DOCUMENTS 8,825,428 B2 * 9/2014 Addison ............ A61B 5/02141
702/98
8,961,185 B2  2/2015 Bleich et al.
(Continued)

FOREIGN PATENT DOCUMENTS

WO  WO 2016/110804 A1  7/2016

OTHER PUBLICATIONS

Yuriy Kurylyak, Smartphone-Based Photoplethysmogram Measurement, 2012 River Publishers. All rights reserved, Digital Image and Signal Processing for Measurement Systems, 135-164. (Year: 2012).*
(Continued)

*Primary Examiner* — Tung S Lau
(74) *Attorney, Agent, or Firm* — Finnegan, Henderson, Farabow, Garrett & Dunner LLP

(57) ABSTRACT

Systems and methods for adaptive sensors calibration are provided. The traditional systems and methods provide for heart rate monitoring using PPG methods but do not focus on adaptive calibration with real-time feedback and dynamic signal quality validation. Embodiments of the present disclosure provide for obtaining an initial value pertaining to a set of calibration parameters of a first sensor and performing a comparison with a pre-defined threshold; incrementing value of the set of calibration parameters by a pre-defined value and performing a comparison; obtaining from the sensor configuration matrix, an initial value pertaining to a set of calibration parameters of a second sensor and performing a comparison; and repeating the steps performed above if the comparisons performed does not match pre-defined quality threshold and finally updating sensor configuration matrix whenever pre-defined quality threshold is matched.

8 Claims, 4 Drawing Sheets

(51) Int. Cl.
*A61B 5/024* (2006.01)
*A61B 5/00* (2006.01)

(52) U.S. Cl.
CPC ........ *A61B 5/14552* (2013.01); *A61B 5/7221* (2013.01); *A61B 2560/0223* (2013.01)

(56) References Cited

U.S. PATENT DOCUMENTS

| | | |
|---|---|---|
| 9,060,695 B2 * | 6/2015 | Peters ................ A61B 5/14552 |
| 9,232,915 B2 | 1/2016 | Chua et al. |
| 2010/0280348 A1 | 11/2010 | Wenzel et al. |
| 2014/0275852 A1 | 9/2014 | Hong et al. |
| 2014/0316305 A1 | 10/2014 | Venkatraman et al. |
| 2016/0220122 A1 * | 8/2016 | Luna ................... A61B 5/1102 |
| 2017/0340209 A1 * | 11/2017 | Klaassen ............... A61B 5/681 |
| 2018/0078156 A1 * | 3/2018 | Chen ................. A61B 5/02125 |
| 2018/0110960 A1 * | 4/2018 | Youngblood ........ A61B 5/0031 |
| 2018/0317782 A1 * | 11/2018 | Ahmed .............. A61B 5/02427 |

OTHER PUBLICATIONS

Garbarino et al., "Empatica E3—A wearable wireless multi-sensor device for real-time computerized biofeedback and data acquisition", IEEE, Wireless Mobile Communication and Healthcare (Mobihealth), 2014 EAI 4th International Conference, pp. 39-42, (2014) https://affect.media.mit.edu/pdfs/14.garbarino-lai-bender-mobihealth.pdf.

Yilmaz et al., "Detecting Vital Signs with Wearable Wireless Sensors", Sensors, vol. 10, issue 12, pp. 10837-10862, (2010) https://affect.media.mit.edu/pdfs/14.garbarino-lai-bender-mobihealth.pdf.

* cited by examiner

SYSTEMS AND METHODS FOR ADAPTIVE SENSORS CALIBRATION

PRIORITY CLAIM

The U.S. patent application claims priority under 35 U.S.C. § 119 to: India Application No. 201721014655, filed on Apr. 25, 2017. The entire contents of the aforementioned application are incorporated herein by reference.

TECHNICAL FIELD

The disclosure herein generally relates to calibration techniques, and, more particularly, to systems and methods for adaptive sensors calibration.

BACKGROUND

Photoplethysmography (PPG) technology has been used to develop small, wearable, pulse rate sensors. These devices, consisting of infrared light-emitting diodes (LEDs) and photodetectors, offer a simple, reliable, low-cost means of monitoring the pulse rate noninvasively. Optical technologies have facilitated the use of high-intensity green LEDs for PPG, increasing the adoption of this measurement technique. Heart rate monitoring using photoplethysmography (PPG) has gained a lot of significance with the development of smart-watches and wristbands for health care and fitness. The PPG based wearable devices however suffer from poor signal quality due to as the PPG mechanism is dependent on LED illumination and diversity in user skin tone. The sensor calibration includes current LED setting, gaining control of analog front-end and LED pulse width variations. One sensor calibration technique may not work for all types of users. Sensor placement is also a major factor that determines PPG signal quality. Still further, the PPG based wearable systems face a major challenge with respect to signal quality validation. The complexity of heart-rate estimation algorithm is thoroughly dependent on the signal quality.

PPG signal quality may lead to lead to significant error in heart rate estimations and related physiological measurements. Hence, there is a need for technology that provides for online signal quality validation with real-time feedback and that further provides for adaptive sensor calibration for a particular user and also stores these parameters for future references.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

Systems and methods of the present disclosure enable adaptive sensors calibration. In an embodiment of the present disclosure, there is provided a method for adaptive sensors calibration, the method comprising: obtaining an initial value pertaining to a set of calibration parameters of a first sensor from a sensor configuration matrix; performing based on the initial value, a comparison of a photoplethysmogram (PPG) signal captured by the first sensor with a pre-defined threshold, characterized in that the output of the PPG signal is based on a position of the first sensor placed on an object; based on the comparison, performing at least one of: (i) updating the calibration parameters in the sensor configuration matrix; (ii) incrementing value of the set of calibration parameters by a pre-defined value and performing a comparison of an output of a photoplethysmogram (PPG) signal captured by the first sensor with a first pre-defined threshold based on the incremented value, characterized in that the output of the PPG signal is based on a position of the first sensor placed on the object; and (iii) obtaining, from the sensor configuration matrix, an initial value pertaining to a set of calibration parameters of a second sensor, and performing a comparison of a photoplethysmogram (PPG) signal captured by the second sensor with a second pre-defined threshold and repeating the steps (i)-(iii), characterized in that the output of the PPG signal is based on a position of the second sensor placed on the object; and generating a report comprising an updated information for each sensor from the sensor configuration matrix for the object.

In an embodiment of the present disclosure, there is provided a system for adaptive sensors calibration, the system comprising one or more processors; one or more data storage devices operatively coupled to the one or more processors and configured to store instructions configured for execution by the one or more processors to: obtain an initial value pertaining to a set of calibration parameters of a first sensor; perform based on the initial value, a comparison of a photoplethysmogram (PPG) signal captured by the first sensor with a pre-defined threshold, characterized in that the output of the PPG signal is based on a position of the first sensor placed on an object; based on the comparison, performing at least one of: (i) update the calibration parameters in the sensor configuration matrix; (ii) increment value of the set of calibration parameters by a pre-defined value and perform a comparison of an output of a photoplethysmogram (PPG) signal captured by the first sensor with a first pre-defined threshold based on the incremented value, characterized in that the output of the PPG signal is based on a position of the first sensor placed on the object; and (iii) obtain from the sensor configuration matrix an initial value pertaining to a set of calibration parameters of a second sensor, and perform a comparison of a photoplethysmogram (PPG) signal captured by the second sensor with a second pre-defined threshold and repeat the steps (i)-(iii), characterized in that the output of the PPG signal is based on a position of the second sensor placed on the object; and generate a report comprising an updated information for each sensor from the sensor configuration matrix for the object.

In an embodiment of the present disclosure, incrementing value of the set of calibration parameters by a pre-defined value until the incremented value reaches a maximum allowable value associated with the set of calibration parameters is performed.

In an embodiment of the present disclosure, the sensor configuration matrix is updated when the output of the photoplethysmogram (PPG) signal matches the predefined threshold.

In an embodiment of the present disclosure, the first pre-defined threshold and the second pre-defined threshold are identical.

In an embodiment of the present disclosure, the first pre-defined threshold and the second pre-defined threshold are different from each other.

In an embodiment of the present disclosure, the first pre-defined threshold and the second pre-defined threshold are based on selection of the set of calibration parameters for each of the first sensor and the second sensor.

In another embodiment herein provides one or more non-transitory machine readable information storage mediums comprising one or more instructions, which when executed by one or more hardware processors perform actions to: obtain an initial value pertaining to a set of calibration parameters of a first sensor; perform based on the initial value, a comparison of a photoplethysmogram (PPG) signal captured by the first sensor with a pre-defined threshold, characterized in that the output of the PPG signal is based on a position of the first sensor placed on an object; based on the comparison, performing at least one of: (i) update the calibration parameters in the sensor configuration matrix; (ii) increment value of the set of calibration parameters by a pre-defined value and perform a comparison of an output of a photoplethysmogram (PPG) signal captured by the first sensor with a first pre-defined threshold based on the incremented value, characterized in that the output of the PPG signal is based on a position of the first sensor placed on the object; and (iii) obtain from the sensor configuration matrix an initial value pertaining to a set of calibration parameters of a second sensor, and perform a comparison of a photoplethysmogram (PPG) signal captured by the second sensor with a second pre-defined threshold and repeat the steps (i)-(iii), characterized in that the output of the PPG signal is based on a position of the second sensor placed on the object; and generate a report comprising an updated information for each sensor from the sensor configuration matrix for the object.

It is to be understood that both the foregoing general description and the following detailed description are exemplary and explanatory only and are not restrictive of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments of the present disclosure provides systems and methods of photoplethysmogram (PPG) signal calibration with real-time feedback for wrist wearable device. PPG signal quality as received from wrist is notorious for poor signal quality. This leads to significant error in heart rate estimations and related physiological measurements. None of the traditional systems and methods have introduced calibration system with real-time feedback. Signal quality has always been considered as signal consistency, none of the traditional systems and methods have tried to study signal quality as a measure of deviation from a gold-standard template in transformed domain. Further, calibration methods have only concentrated on power consumption and have not provided enough attention to quality and personalized parameter reference. Still further, the traditional systems and methods do not consider different wavelength effect on diverse skin tone together and consider that user only wear the device in conventional manner which causes a major limitation to the ergonomics of the wearable.

Hence there is a need for adaptive sensor calibration for selecting the optimal wavelength, sensor position and calibration for a particular user. Further, there is a need for dynamic signal validation system and method which provides for signal quality check against the adaptive calibration.

Figure 1:
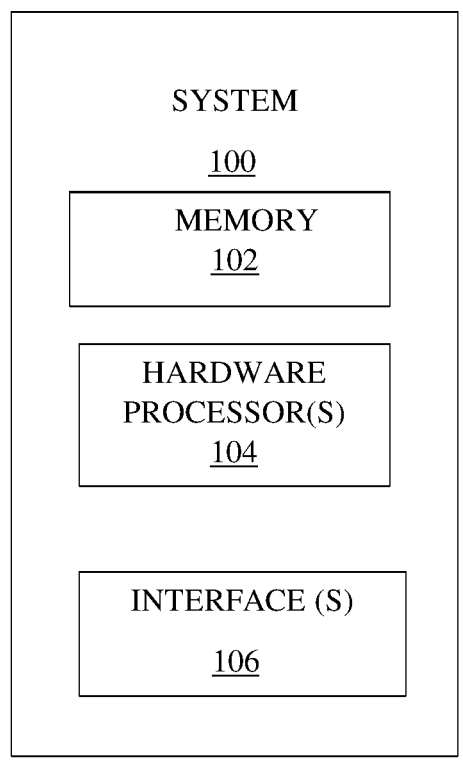
FIG. 1 illustrates a block diagram of a system for adaptive sensors calibration according to an embodiment of the present disclosure.
Figure 2:
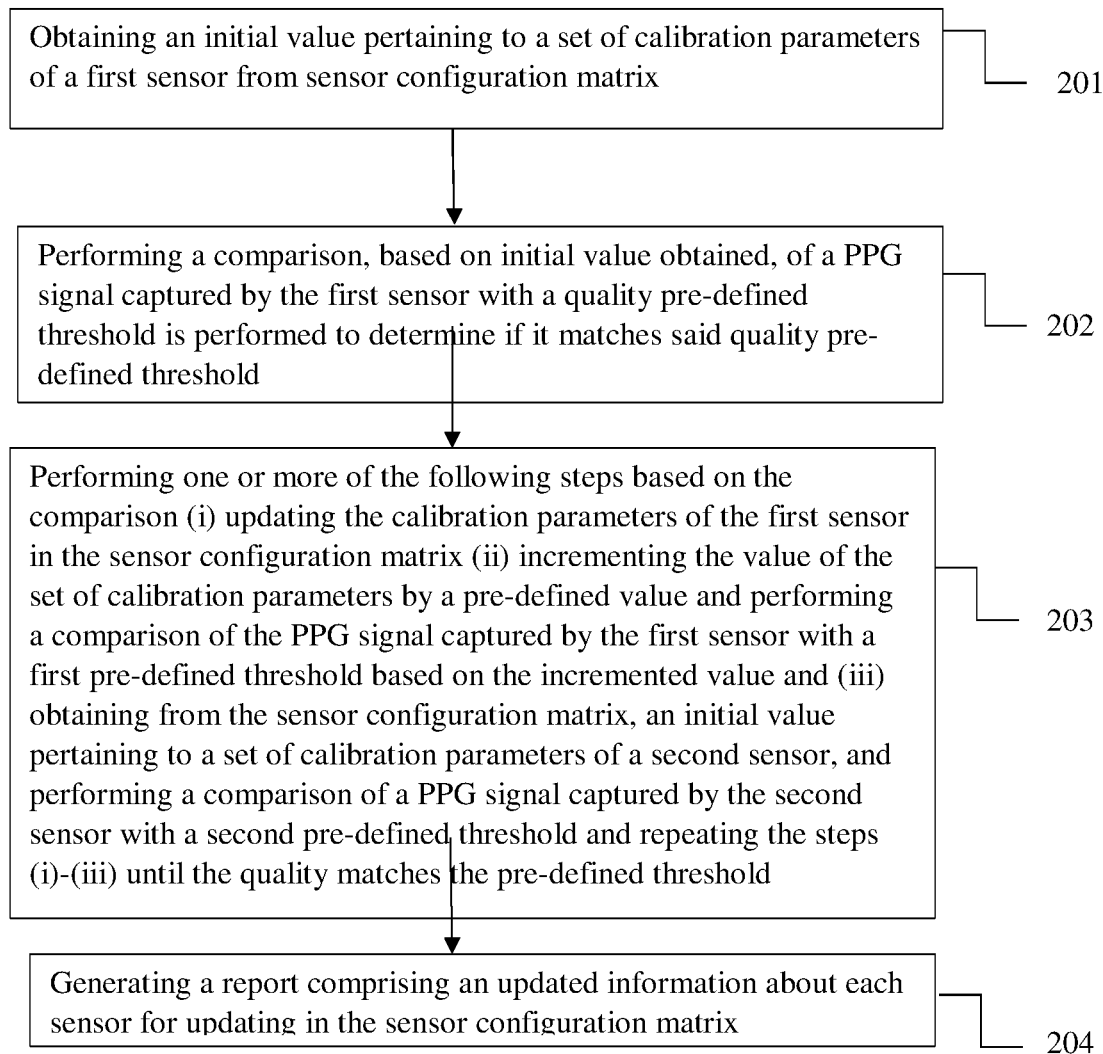
FIG. 2 illustrates a flowchart illustrating the steps involved for adaptive sensors calibration according to an embodiment of the present disclosure; and FIG. 3A through FIG. 3B illustrates a flowchart of a method for calibrating one or more sensors according to an embodiment of the present disclosure.

Referring now to the drawings, and more particularly to FIG. 1 through 2, where similar reference characters denote corresponding features consistently throughout the figures, there are shown preferred embodiments and these embodiments are described in the context of the following exemplary system and/or method.

FIG. 1 illustrates an exemplary block diagram of a system 100 for calibrating one or more sensors according to an embodiment of the present disclosure.

In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or nonvolatile memory, such as read only memory (ROM), erasable programmable ROM, flash memories, hard disks, optical disks, and magnetic tapes. In an embodiment, one or more modules (not shown) of the system 100 can be stored in the memory 102.

FIG. 2, with reference to FIG. 1, illustrates an exemplary flow diagram of a method for calibrating one or more sensors according to an embodiment of the present disclosure. In an embodiment the system 100 comprises one or more data storage devices of the memory 102 operatively coupled to the one or more hardware processors 104 and is configured to store instructions for execution of steps of the method by the one or more processors 104. In an embodiment of the present disclosure, the one or more sensors for which adaptive calibration is performed, may be associated with (or integrated within) a wearable device (eg. a smart watch, a wrist band, fitness band and the like). The steps of the method of the present disclosure will now be explained with reference to the components of the device 100 as depicted in FIG. 1 and the flow diagram. In the embodiments of the present disclosure, the hardware processors 104 when configured the instructions performs one or more methodologies described herein. In an embodiment of the present disclosure, at step 201, the one or more hardware processors 104 obtain an initial value pertaining to a set of calibration parameters of a first sensor. At step 202, the one or more hardware processors 104 perform a comparison of a photoplethysmogram (PPG) signal captured by the first sensor with a quality pre-defined threshold. In an embodiment of the present disclosure, the initial value being set to the first sensor, quality of the PPG signal (which is an output of the first sensor) may be compared with a pre-defined quality. In an embodiment, quality of the PPG signal may be referred as PPG signal coefficient that is compared with the pre-defined threshold (or pre-defined coefficient). The PPG signal may be captured upon attaching the first sensor to an object (e.g., a user). At step 203, based on the comparison, the one or more hardware processors 104 (i) update calibration parameters of the first sensor in the sensor configuration matrix; (ii) increment value of the set of calibration parameters by a pre-defined value and perform a comparison of a photoplethysmogram (PPG) signal captured by the first sensor with a first pre-defined threshold based on the incremented value, characterized in that the output of the PPG signal is based on a position of the first sensor placed on the object, and (iii) obtain from the sensor configuration matrix an initial value pertaining to a set of calibration parameters of a second sensor, and perform a comparison of a photoplethysmogram (PPG) signal captured by the second sensor with a second pre-defined threshold and repeat the steps (i)-(iii), characterized in that the output of the PPG signal is based on a position of the second sensor placed on the object. In an embodiment of the present disclosure, the calibration parameters are updated in the sensor configuration matrix when the photoplethysmogram (PPG) signal captured by the first sensor matches the pre-defined threshold. Else (if characteristic of the PPG signal do not match the pre-defined threshold), the initial value (e.g., 1.0) of the set of calibration parameters is incremented by a pre-defined value (e.g., 2.0) and the step of performing comparison is repeated. This step of (i) incrementing value of the set of calibration parameters to a pre-defined value and (ii) performing the comparison are repeated until the incremented value reaches a maximum allowable value associated with the set of calibration parameters. For example, if the maximum allowable value associated with the set of calibration parameters is 5.0, then value of the set of calibration parameters may be incremented by the pre-defined value (e.g., from 1.0 to 2.0, 2.0 to 3.0, 3.0 to 4.0, and 4.0 to 5.0) and the comparison is performed accordingly. If the increment value reaches to the maximum allowable value and the characteristic of the PPG signal (e.g., quality of the PPG signal) does not match with a pre-defined threshold for the set of calibration parameters, then the hardware processors 104 obtain, from the sensor configuration matrix stored in the memory 102, an initial value pertaining to a set of calibration parameters of a second sensor and the steps (i)-(iii) are repeated. At step 204, a report comprising an updated information for each sensor for the object is generated. The above steps of selecting a best sensor from an array of sensors may be better understood by way of following example. Suppose we have two PPG sensors namely, PPG1 and PPG2 and acceptable pre-defined threshold as 0.7. For PPG1 the PPG signal coefficient obtained by performing the discrete wavelet transform is −0.22518 and the pre-defined threshold is −1.0769, the error is 0.7254269584. Hence, the quality matches the pre-defined threshold. It will be updated in sensor configuration matrix. However, suppose the PPG signal coefficient obtained is −17.573 and the pre-defined threshold is −21.069, the error is 12.222016. Hence, the quality does not match the pre-defined threshold. Now the PPG signal coefficients get incremented by a pre-defined value to −17.498. Pre-defined threshold is −15.453. The error is 4.182025. Again, the quality does not matches the acceptable threshold which is 0.7. Again, the photoplethysmogram (PPG) signal coefficients get incremented by a pre-defined value to −16.494. Pre-defined threshold is −6.7799. The error is 94.36373881 which is again a mismatch. Hence, the photoplethysmogram (PPG) signal coefficients get incremented and keep incrementing until they reach the maximum allowable value. Now suppose the estimated threshold reference computed for PPG1 by performing discrete wavelet transform on obtained coefficients is 0.3036216903. The above steps may be repeated for PPG2 and suppose the estimated threshold reference computed for PPG2 by performing discrete wavelet transform on obtained coefficients is 0.8847139775. Hence PPG1 will be selected as the computed threshold is less than the pre-defined acceptable threshold and the parameters may be stored in the sensor configuration matrix. PPG2 will be rejected as it's computed threshold is greater than the pre-defined acceptable threshold. According to an embodiment of the present disclosure, the first pre-defined threshold and the second pre-defined threshold may be identical or different from each other and are based on the selection of the set of calibration parameters for each of the first and the second sensor.

FIG. 3A through FIG. 3B, with respect to FIGS. 1-2, illustrates an exemplary flow diagram of a method for calibrating one or more sensors according to an embodiment of the present disclosure. At step 301, the one or more hardware processors 104 obtain an initial value pertaining to a set of calibration parameters of a first sensor. In an embodiment, the initial value pertaining to the set of calibration parameters is obtained from a sensor configuration matrix stored in the memory 102. At step 302, the one or more hardware processors 104 perform a comparison of a photoplethysmogram (PPG) signal captured by the first sensor with a pre-defined threshold. At step 303, the one or more hardware processors 104 determine whether a match is found between the photoplethysmogram (PPG) signal captured by the first sensor with the pre-defined threshold. If a match is found between the photoplethysmogram (PPG) signal captured by the first sensor with the pre-defined threshold, the sensor configuration matrix is updated with the matched details, at step 304. At step 305, the one or more hardware processors 104 check whether there are any further sensor(s) available for calibration. If further sensors are available, (if yes), at step 306, the one or more hardware processors 104 obtain an initial value of a set of calibration parameters for a second sensor, and the step 302 is repeated. Else, (if there are no further sensor(s) available, the process is terminated.

In an embodiment of the present disclosure, referring to step 307, if there is no match found between the photoplethysmogram (PPG) signal captured by the first sensor with the pre-defined threshold, the one or more hardware processor 104 determine whether the initial value has reached the maximum allowable value. If the initial value has reached the maximum allowable value (if yes), the one or more hardware processors 104 repeat the step 305. Else (if the initial value has not reached the maximum allowable value, the initial value is incremented to a next pre-define value at step 308, and the step 302 is repeated.

Figure 3:
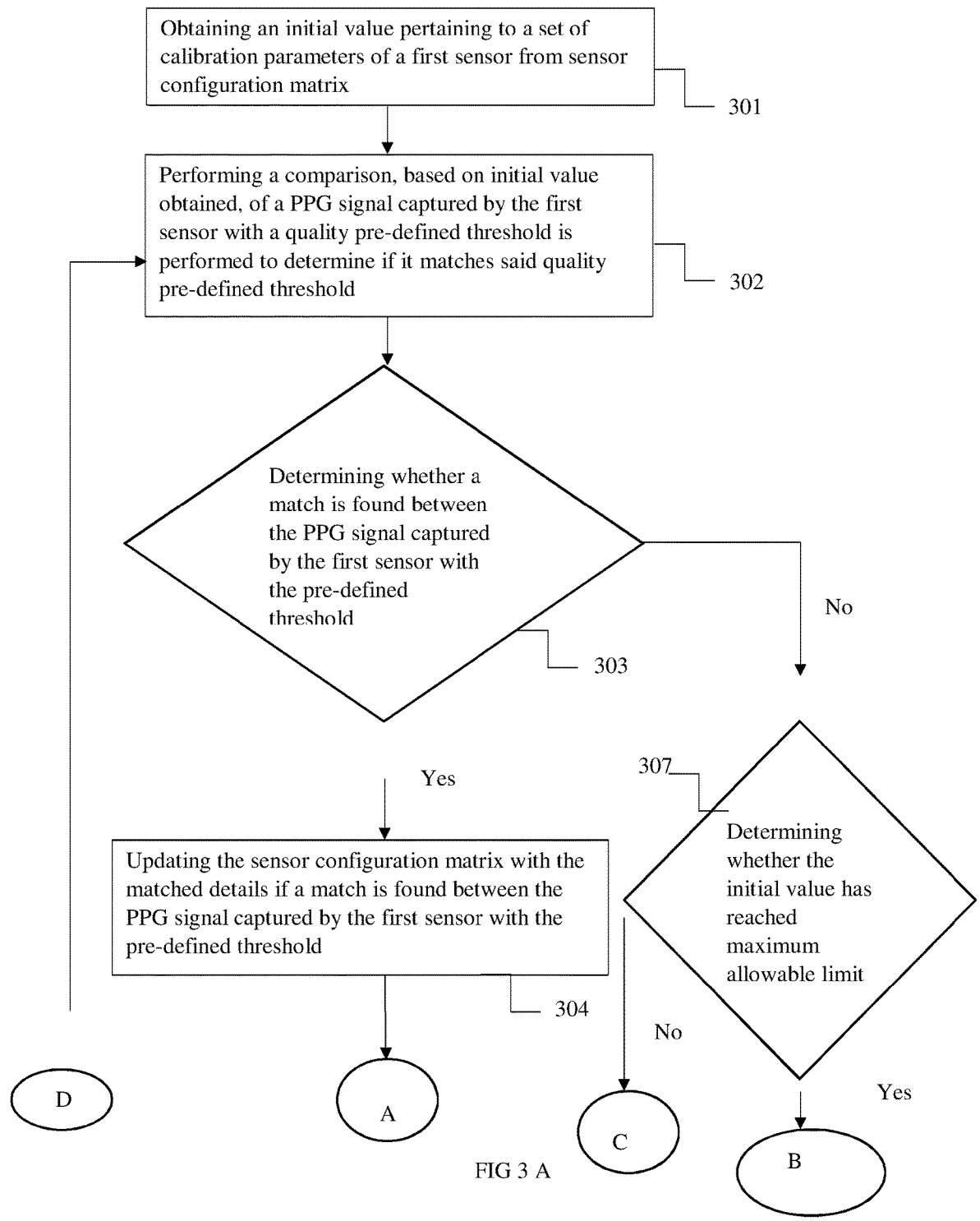
Figure 3:
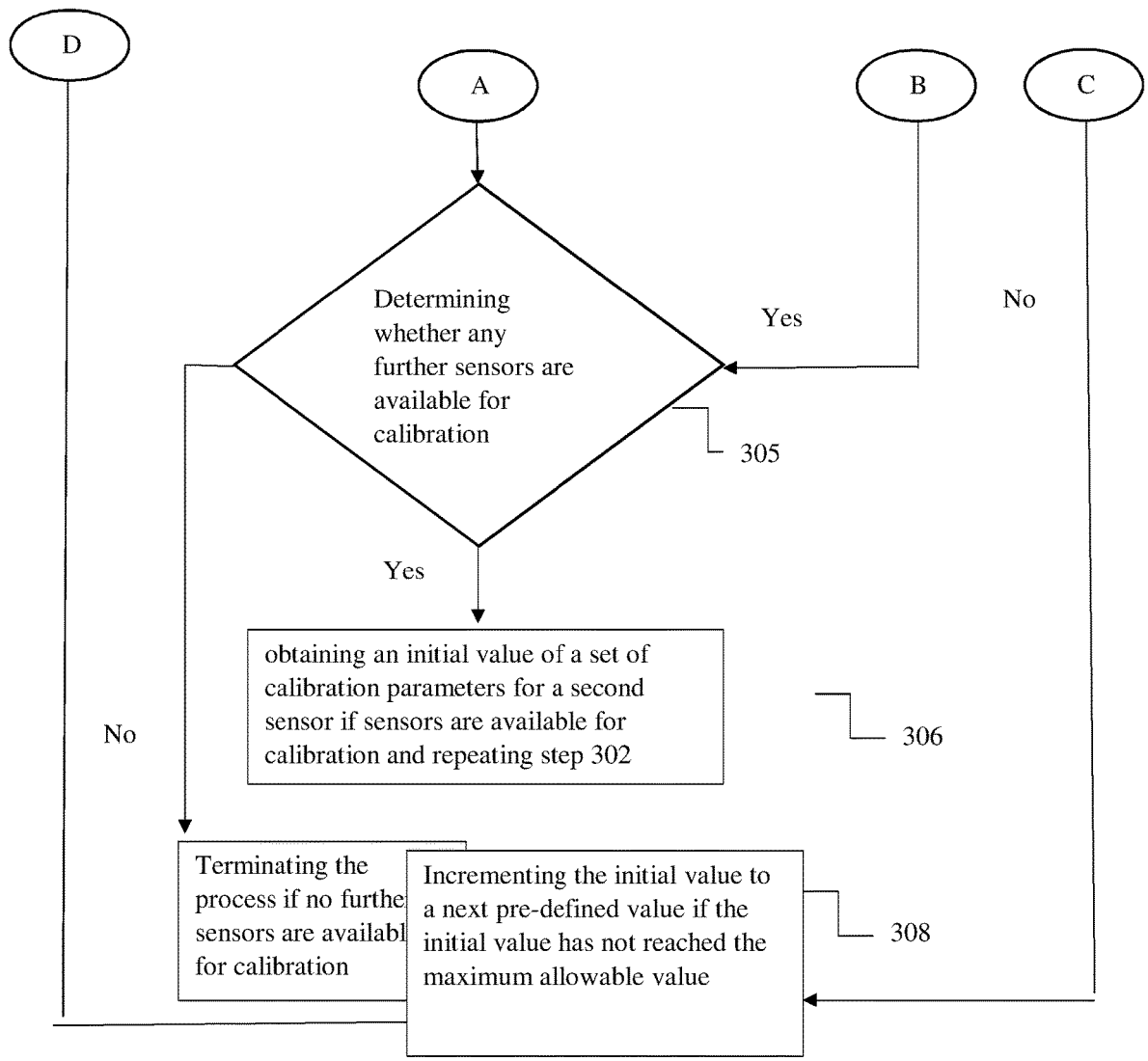

The embodiments of the present disclosure are better understood by way of examples, as illustrated below:

In an embodiment of present disclosure, referring to FIGS. 2-3B, the initial value pertaining to a set of calibration parameters of a first sensor may be obtained from a sensor configuration matrix (not shown in memory 106 of the system 100) stored in the memory 106 of the system 100. Based on the initial value obtained, a comparison of a photoplethysmogram (PPG) signal coefficient captured by the first sensor with a template photoplethysmogram (PPG) coefficients comprising of pre-defined threshold may be performed to validate quality of the photoplethysmogram (PPG) signal. The first sensor and the sensor configuration matrix are executed by the system 100 and may be stored in the memory 102. Suppose the acceptable pre-defined threshold is 0.7. Referring to Table 1 below, if photoplethysmogram (PPG) signal coefficient obtained denoted by X1 is −0.22518 and the pre-defined threshold denoted by Y1 is −1.0769, the error is 0.7254269584. Hence, the quality matches the pre-defined threshold.

TABLE 1

| Photoplethysmogram (PPG) signal sensor captured coefficient denoted by X | Template photoplethysmogram (PPG) coefficients/Pre-defined threshold denoted by Y | Error computed using weighted sum of square technique as (Y1 − X1) * (Y1 − X1) |
|---|---|---|
| −0.22518 (X1) | −1.0769 (Y1) | 0.7254269584 |

Further, if the quality matches the pre-defined threshold, the photoplethysmogram (PPG signal) and associated calibration parameters are updated in the sensor configuration matrix for optimal performance. Hence, the above parameters may be stored as personalized parameters in sensor configuration matrix for future references. While one of the photoplethysmogram (PPG) sensor and it's parameters are chosen, all other sensors in sensor configuration matrix may not be utilized, to maximize the power consumption.

In an embodiment of present disclosure, based on the above comparison performed between the photoplethysmogram (PPG) signal captured by the first sensor with a pre-defined threshold, if quality does not match the pre-defined threshold, all calibration parameters or photoplethysmogram (PPG) signal coefficients may be incremented by pre-defined values stored in the system 100 and a comparison of a photoplethysmogram (PPG) signal captured by the first sensor with a first pre-defined threshold or template photoplethysmogram (PPG) coefficients based on the incremented value may further be performed for validating quality of the photoplethysmogram (PPG) signal. Suppose the acceptable pre-defined threshold is 0.7. Referring to Table 2 below, if photoplethysmogram (PPG) signal coefficient obtained denoted by X1 is −17.573 and the pre-defined threshold denoted by Y1 is −21.069, the error is 12.222016. Hence, the quality does not match the pre-defined threshold. Now the photoplethysmogram (PPG) signal coefficients get incremented by a pre-defined value to −17.498 denoted by X2. Pre-defined threshold denoted by Y2 is −15.453. The error is 4.182025. Again, the quality does not matches the threshold which is 0.7. Again, the photoplethysmogram (PPG) signal coefficients get incremented by a pre-defined value to −16.494 denoted by X3. Pre-defined threshold denoted by Y3 is −6.7799. The error is 94.36373881 which is again a mismatch. Hence, the photoplethysmogram (PPG) signal coefficients get incremented and keep incrementing until they reach the value −0.22518 denoted by X4. The threshold denoted by Y4 is −1.0769. The error is computed as 0.7254269584 which matches the pre-defined threshold. Hence the quality matches with pre-defined threshold.

TABLE 2

| Photoplethysmogram (PPG) signal sensor captured coefficient denoted by X | Template photoplethysmogram (PPG) coefficients/Pre-defined threshold denoted by Y | Error computed using weighted sum of square technique as (Y − X) * (Y − X) |
|---|---|---|
| −17.573 (X1) | −21.069 (Y1) | 12.222016 computed as (Y1 − X1) * (Y1 − X1) |
| −17.498 (X2) | −15.453 (Y2) | 4.182025 computed as (Y2 − X2) * (Y2 − X2) |
| −16.494 (X3) | −6.7799 (Y3) | 94.36373881 computed as (Y3 − X3) * (Y3 − X3) |
| −0.22518 (X4) | −1.0769 (Y4) | 0.7254269584 computed as (Y4 − X4) * (Y4 − X4) |

Again, once the quality matches the pre-defined threshold, the PPG signal and associated calibration parameters are updated in the sensor configuration matrix for optimal performance.

In an embodiment of present disclosure, based on the above comparison performed after incrementing all calibration parameters with pre-defined values, if the quality of photoplethysmogram (PPG) signal does not match with the pre-defined threshold, an initial value pertaining to a set of calibration parameters of a second sensor may be obtained and a comparison of a photoplethysmogram (PPG) signal captured by the second sensor with a second pre-defined threshold may again be performed for validating quality of the photoplethysmogram (PPG) signal. The second sensor is executed by the system 100 and may be stored in the memory 102. Thus, if the sensor calibration reaches to maximum value without matching the quality criteria even after incrementing with pre-defined values, the calibration starts with secondary sensors. Again, let the pre-defined quality acceptable threshold is 0.7. Referring to Table 3 below, suppose that after comparison performed at the previous step, quality of photoplethysmogram (PPG) signal does not still match with the pre-defined threshold, a comparison of a photoplethysmogram (PPG) signal captured by the second sensor with a second pre-defined threshold may be performed. Now if photoplethysmogram (PPG) signal coefficient obtained denoted by X1 is −0.22518 and the pre-defined threshold denoted by Y1 is −1.0769, the error as 0.7254269584. This matches the acceptable threshold and hence the photoplethysmogram (PPG) signal quality matches.

TABLE 3

| Photo-plethysmogram (PPG) signal sensor captured coefficient denoted by X | Template photo-plethysmogram (PPG) coefficients/Pre-defined threshold denoted by Y | Error computed using weighted sum of square technique as (Y − X) * (Y − X) |
|---|---|---|
| −0.22518 (X4) | −1.0769 (Y4) | 0.7254269584 computed as (Y4 − X4) * (Y4 − X4) |

Further, once the quality matches the pre-defined threshold, the PPG signal and associated calibration parameters are updated in the sensor configuration matrix for optimal performance. Hence the above values may be stored in sensor configuration matrix.

In an embodiment of present disclosure, based on above comparison performed, if quality of the photoplethysmogram (PPG) signal still does not match with the pre-defined threshold, the above steps may be repeated for all photoplethysmogram (PPG) sensors until the photoplethysmogram (PPG) signal matches pre-defined quality threshold. After repeating the steps, if there are further sensors available for calibration, the photoplethysmogram (PPG) signal coefficients for a second sensor is obtained, compared with pre-defined template threshold. The sensor configuration matrix may be updated if the signal quality matches the pre-defined template threshold. If there are no further sensors available for calibration, the calibration parameters may be incremented with defined values if required and again compared with pre-defined template threshold in the same manner as above until it matches the quality criteria. The photoplethysmogram (PPG) signal and associated calibration parameters may then be updated in the sensor configuration matrix for optimal performance upon matching pre-defined quality threshold. While one of the photoplethysmogram (PPG) sensor and it's parameters are chosen, all other sensors in sensor configuration matrix are not utilized, to maximize the power consumption. The present disclosure thus, owing to this closed loop feedback system, facilitates optimal photoplethysmogram (PPG) sensor position and overall performance.

According to an embodiment of the present disclosure referring to table 4, detailed computation from raw PPG signals of whether the computed signal is usable or not may now be considered. Acceptable pre-defined threshold may again be assumed to be 0.7.

TABLE 4

| PPG Sensors (Column A) | Raw PPG wavelet coefficients (Column B) | Reference PPG wavelet coefficients (Column C) | Error computed between acquired or measured and referenced PPG signal (column D) using weighted sum of square technique |
|---|---|---|---|
| SENSOR-1 GREEN WAVE-LENGTH | −17.573 | −21.069 | 12.222016 |
| | −17.498 | −15.453 | 4.182025 |
| | −16.494 | −6.7799 | 94.36373881 |
| | −14.543 | 4.2713 | 353.97788449 |

TABLE 4-continued

| PPG Sensors (Column A) | Raw PPG wavelet coefficients (Column B) | Reference PPG wavelet coefficients (Column C) | Error computed between acquired or measured and referenced PPG signal (column D) using weighted sum of square technique |
|---|---|---|---|
| | −11.753 | 16.49 | 797.667049 |
| | 0.13402 | −1.0017 | 1.2898599184 |
| | −0.13293 | −1.804 | 2.7924749449 |
| | −0.38284 | −2.511 | 4.5290649856 |
| | −0.59917 | −2.9761 | 5.6497962249 |
| | −0.79534 | −3.0833 | 5.2347609616 |
| | 0.086402 | −0.28367 | 0.1369532852 |
| | 0.011807 | −0.42522 | 0.1909925987 |
| | −0.03526 | −0.56826 | 0.284089 |
| | −0.055794 | −0.70628 | 0.4231320362 |
| | −0.1182 | −0.83251 | 0.5102387761 |
| | −0.14708 | −0.9403 | 0.6291979684 |
| | −0.19578 | −1.0235 | 0.6851203984 |
| | −0.22518 | −1.0769 | 0.7254269584 |
| | −0.26738 | −1.0963 | 0.6871083664 |
| | −0.29333 | −1.0793 | 0.6177488409 |
| SENSOR-2 RED WAVE-LENGTH | −19.3171474079 | −21.069 | 3.0689875046 |
| | −23.1125876788 | −15.453 | 58.669283409 |
| | −19.4856823253 | −6.7799 | 161.4369044973 |
| | −18.5374344577 | 4.2713 | 520.2383675607 |
| | −12.6458725679 | 16.49 | 848.8990702939 |
| | −0.3056032866 | −1.0017 | 0.4845506344 |
| | −1.0923403048 | −1.804 | 0.5064595218 |
| | −0.6592699509 | −2.511 | 3.4289041747 |
| | −1.200718479 | −2.9761 | 3.1519795452 |
| | −2.8232792445 | −3.0833 | 0.0676107933 |
| | −2.305393477 | −.028367 | 4.0873658173 |
| | −0.5017591753 | −0.42522 | 0.0058582454 |
| | −3.8317937553 | −0.56826 | 10.6506525717 |
| | −3.8988471325 | −0.70628 | 10.1924848953 |
| | −4.1824316047 | −0.83251 | 11.2219747576 |
| | −1.0071125206 | −0.9403 | 0.0044639129 |
| | −4.1963487055 | −1.0235 | 10.0669689079 |
| | −4.7035756764 | −1.0769 | 13.1527764621 |
| | −2.184963847 | −1.0963 | 1.1851889718 |
| | −2.6778883646 | −1.0793 | 2.55548 |

Referring to table 4 again, how the present disclosure chooses the best sensor from an array of sensors and performs dynamic real-time signal quality validation may now be understood. Two wavelengths, namely, red and green are applied on the same user without changing the current settings. Wavelet transform is applied on the raw PPG signals to determine coefficients as shown in column B. The referenced PPG signals may then be obtained by applying Gaussian approximation to PPG signals and then applying wavelet decomposition to these approximated PPG signals. The referenced coefficients are shown in column C and these may be further stored in the memory 102 of the system 100 as features of a particular user. The error between the referenced and the acquired or measured PPG signal may then be computed as depicted in column D. The error is computed using one or more weighted sum of squares (SS) method (s)/technique(s) with all weight equal to 1. It is because Euclidean distance is used as a measure of error. In an embodiment of the present disclosure, the sum of square may be used as valid error measurement. Hence the error in column D may be calculated referring to the first row or first set of values as (−17.573−(−21.069))^2=12.222016. The error in column D for the remaining rows or remaining set of values may be calculated in the same way.

The intermediate error calculation may be computed as the average error (computed between referenced and measured or acquired PPG signals) of different coefficients in column D. Hence, for green wavelength PPG sensor, average error of first 5 coefficients in column D may be computed as 252.48254266. Similarly, average error of next 5 coefficients and final 10 coefficients in column D may be computed as 3.8991914071 and 0.4890008229 respectively. For red wavelength PPG sensor, average error of first 5 coefficients in column D may be computed as 318.4625226531. Similarly, average error of next 5 coefficients and final 10 coefficients in column D may be computed as 1.5279009339 and 6.3123219301 respectively. According to an embodiment of the invention referring to table 4, the estimated threshold with respect to reference signal for both the sensors (green and red) may then be computed using discrete wavelet transform technique on the raw PPG signals in column B to obtain approximated PPG signals. Hence using discrete wavelet transform the estimated threshold for green wavelength PPG sensor is 0.3036216903 and for red wavelength is 0.8847139775. The acceptable predefined threshold is 0.7 as mentioned above. It may be observed that for green wavelength PPG sensor the estimated error threshold is 0.3036216903 and is less than predefined error threshold which is 0.7 and hence is acceptable. For the red wavelength, the estimated error threshold 0.8847139775 and is greater than predefined error threshold which is 0.7 and hence not acceptable.

The present disclosure thus facilitates autonomous and adaptive sensor calibration by choosing the nest sensor from an array of sensors and implements multi wavelengths instead of a single wavelength so that an optimum settings for a user may be stored. Referring to table 4 again, if the red wavelength is not chosen for a particular user this may be stored in the memory 102 of the system 100 so that the system 100 increases the current settings or calibration parameters or selects a green wavelength when next time a user puts on the wearable device. Thus the present disclosure facilitates real-time feedback.

According to an embodiment of present disclosure, the validation of photoplethysmogram (PPG) signal is performed by a photoplethysmogram (PPG) signal quality validation algorithm. The details of photoplethysmogram (PPG) signal validation technique may now be considered. The wavelength decomposition may be implemented and the coefficients of reference photoplethysmogram (PPG) signal discussed below may then be compared with coefficients of measured or acquired photoplethysmogram (PPG) signal from photoplethysmogram (PPG) sensors for validation. The error between the coefficients of measured or acquired and referenced photoplethysmogram (PPG) signals may further be computed.

The Gaussian approximation of photoplethysmogram (PPG) signals may first be performed in the following way for computing the coefficients of referenced photoplethysmogram (PPG) signal:

Let the reference signal be denoted as $R_{PPG}(t)$.

$$R_{PPG}(t) = A*f_1(t) + B*f_2(t)$$

$f_1(t)$ and $f_2(t)$ are Gaussian basis. A and B are the parameters need to be tuned. The error residual may be defined as:

$$E = R_{PPG}(t) - (A*f_1(t) + B*f_2(t))$$

A and B are chosen by minimizing the RMS of the error residual computed above. Hence, the referenced photoplethysmogram (PPG) signal may be represented by the Gaussian approximation as:

$$A*f_1(t) + B*f_2(t)$$

The wavelength decomposition may then be applied to the above approximated referenced photoplethysmogram (PPG) signal to compute wavelet coefficients of referenced photoplethysmogram (PPG) signal and the wavelength coefficients computed may further be stored in the memory 106 of the system 102 above for future references.

The measured or acquired photoplethysmogram (PPG) signal coefficients may be computed by applying dynamic time wrapping algorithm to the photoplethysmogram (PPG) signal obtained above from photoplethysmogram (PPG) sensor. The Gaussian approximation may then be applied to decompose the time wrapped photoplethysmogram (PPG) signal into sum of two Gaussian functions. The discrete wavelength transform may further be applied to these approximated photoplethysmogram (PPG) signal to compute the wavelet coefficients.

The computed coefficients of measured or acquired and referenced photoplethysmogram (PPG) signal may then be compared. The error between the coefficients of measured or acquired and referenced photoplethysmogram (PPG) signals may further be computed using weighted sum of squares (SS). The weights for the coefficients may be described as in Table 5 below:

TABLE 5

| Wavelet Coefficient's weight distribution | |
|---|---|
| Wavelet coefficient | Weight |
| L1 (level 1 approximation) | .7 |
| LH2 (level 1 approximation) | .2 |
| HH2 (level 2 details) | .1 |

The photoplethysmogram (PPG) signal may finally be accepted when the normalized error is lower than the predefined threshold.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, BLU-RAYs, flash drives, disks, and any other known physical storage media.

It is intended that the disclosure and examples be considered as exemplary only, with a true scope and spirit of disclosed embodiments being indicated by the following claims.

What is claimed is:

1. A system (100) comprising:
a memory(102) storing instructions;
one or more communication interfaces (106); and
one or more hardware processors (104) coupled to the memory (102) via the one or more communication interfaces (106), wherein the one or more hardware processors (104) are configured by the instructions to:
obtain an initial value pertaining to a set of calibration parameters of a first sensor,
perform based on the initial value, a comparison of a photoplethysmogram (PPG) signal captured by the first sensor with a pre-defined threshold, characterized in that the output of the PPG signal is based on a position of the first sensor placed on an object,
based on the comparison, performing at least one of:
(i) update the calibration parameters in the sensor configuration matrix, wherein the calibration parameters are updated in the sensor configuration matrix when the PPG signal captured by the first sensor matches the pre-defined threshold;
(ii) determine whether the initial value pertaining to the set of calibration parameters reached a predefined limit when the PPG signal captured by the first sensor does not match the pre-defined threshold, increment value of the set of calibration parameters by a pre-defined value when the initial value does not reach the predefined limit and perform a comparison of an output of a photoplethysmogram (PPG) signal captured by the first sensor with a first pre-defined threshold based on the incremented value, characterized in that the output of the PPG signal is based on a position of the first sensor placed on the object, wherein the step of (a) incrementing the initial value of the set of calibration parameters to a pre-defined value and (b) performing the comparison are repeated until the incremented value reaches the predefined limit associated with the set of calibration parameters; and
(iii) obtain from the sensor configuration matrix an initial value pertaining to a set of calibration parameters of a second sensor when one of (a) the calibrated parameters are updated and (b) the initial value of the set of calibration parameters reach the predefined limit, and perform a comparison of a photoplethysmogram (PPG) signal captured by the second sensor with a second pre-defined threshold and repeat the steps (i)-(iii), characterized in that the output of the PPG signal is based on a position of the second sensor placed on the object; and
generate a report comprising an updated information for each sensor from the sensor configuration matrix for the object.

2. The system (100) of claim 1, wherein the first pre-defined threshold and the second pre-defined threshold are identical.

3. The system (100) of claim 1, wherein the first pre-defined threshold and the second pre-defined threshold are different from each other.

4. The system (100) of claim 1, wherein the first pre-defined threshold and the second pre-defined threshold are based on selection of the set of calibration parameters for each of the first sensor and the second sensor.

5. One or more non-transitory machine readable information storage mediums comprising one or more instructions which when executed by one or more hardware processors perform actions comprising:
obtaining, from a sensor configuration matrix, an initial value pertaining to a set of calibration parameters of a first sensor;
performing, based on the initial value, a comparison of a photoplethysmogram (PPG) signal captured by the first sensor with a pre-defined threshold, characterized in that the output of the PPG signal is based on a position of the first sensor placed on an object;
based on the comparison, performing at least one of:
(i) updating the calibration parameters in the sensor configuration matrix, wherein the calibration parameters are updated in the sensor configuration matrix when the PPG signal captured by the first sensor matches the pre-defined threshold;

(ii) determining whether the initial value pertaining to the set of calibration parameters reached a predefined limit when the PPG signal captured by the first sensor does not match the pre-defined threshold, incrementing value of the set of calibration parameters by a pre-defined value when the initial value does not reach the predefined limit and performing a comparison of an output of a photoplethysmogram (PPG) signal captured by the first sensor with a first pre-defined threshold based on the incremented value, characterized in that the output of the PPG signal is based on a position of the first sensor placed on the object, wherein the step of (a) incrementing the initial value of the set of calibration parameters to a pre-defined value and (b) performing the comparison are repeated until the incremented value reaches the predefined limit associated with the set of calibration parameters; and (iii) obtaining, from the sensor configuration matrix, an initial value pertaining to a set of calibration parameters of a second sensor when one of (a) the calibrated parameters are updated and (b) the initial value of the set of calibration parameters reach the predefined limit, and performing a comparison of a photoplethysmogram (PPG) signal captured by the second sensor with a second pre-defined threshold and repeating the steps (i)-(iii), characterized in that the output of the PPG signal is based on a position of the second sensor placed on the object; and generating a report comprising an updated information for each sensor from the sensor configuration matrix for the object.

6. The one or more non-transitory machine readable information storage mediums of claim 5, wherein the first pre-defined threshold and the second pre-defined threshold are identical.

7. The one or more non-transitory machine readable information storage mediums of claim 5, wherein the first pre-defined threshold and the second pre-defined threshold are different from each other.

8. The one or more non-transitory machine readable information storage mediums of claim 5, wherein the first pre-defined threshold and the second pre-defined threshold are based on selection of the set of calibration parameters for each of the first sensor and the second sensor.

* * * * *